United States Patent
De Bruijne et al.

(10) Patent No.: US 8,126,240 B2
(45) Date of Patent: Feb. 28, 2012

(54) VERTEBRAL FRACTURE QUANTIFICATION

(75) Inventors: Marleen De Bruijne, Copenhagen (DK); Michael Lund, Copenhagen (DK); Mads Nielsen, Dragor (DK); Paola Pettersen, Vallø (IT)

(73) Assignee: Synarc, Inc., Newark, CA (US)

( * ) Notice: Subject to any disclaimer, the term of this patent is extended or adjusted under 35 U.S.C. 154(b) by 961 days.

(21) Appl. No.: 11/884,166

(22) PCT Filed: Feb. 16, 2006

(86) PCT No.: PCT/EP2006/001407
§ 371 (c)(1),
(2), (4) Date: May 12, 2008

(87) PCT Pub. No.: WO2006/087190
PCT Pub. Date: Aug. 24, 2006

(65) Prior Publication Data
US 2008/0216845 A1  Sep. 11, 2008

(30) Foreign Application Priority Data

Feb. 16, 2005 (GB) .................................. 0503236.2

(51) Int. Cl.
*A61B 19/00* (2006.01)
(52) U.S. Cl. ....................................... 382/131; 382/128
(58) Field of Classification Search .............. 378/4, 901; 382/131, 128
See application file for complete search history.

(56) References Cited

U.S. PATENT DOCUMENTS 5,481,587 A  1/1996  Mazess et al.
6,438,201 B1 *  8/2002  Mazess et al. .................. 378/56

FOREIGN PATENT DOCUMENTS

EP  1 400 203 A  3/2004

OTHER PUBLICATIONS

Smyth et al., "Vertebral Shape: Automatic Measurement with Active Shape Models", *Radiology*, pp. 571-578 (May 1999).
T. Cootes et al., "Active Shape Models—Their Training and Application", *Computer Vision and Image Understanding*, vol. 61, No. 1, pp. 38-59 (1995).
G. Zamora et al., "Hierarchical Segmentation of Vertegrae from X-ray Images", *Proc. of SPIE*, vol. 5032, pp. 631-641 (2003).
A.P. Dempster et al., "Maximum Likelihood from Incomplete Data via the EM Algorithm", *Journal of the Royal Statistical Society*, Series 13, pp. 1-38 (1977).

* cited by examiner

*Primary Examiner* — Hoon Song
(74) *Attorney, Agent, or Firm* — Edwards Wildman Palmer LLP; Peter C. Lauro, Esq.

(57) ABSTRACT

A method of deriving an estimate of the extent of fracture in a vertebra shown in an image of part of A spine is provided. The images of at least two vertebrae are segmented to obtain data representative of the shape and size of each of the vertebrae. An approximation of the shape of a first of the vertebrae is reconstructed by comparing the data obtained for a second of the two vertebrae with a mathematical model of at least the same two vertebrae of an unfractured spine. The unfractured shape of the first vertebra is predicted to enable a comparison of the shape and size of the first vertebra as imaged with the predicted unfractured shape and size. The difference between the respective images is subsequently computed to obtain a result representative of the extent of fracture in the first vertebra.

12 Claims, 5 Drawing Sheets

VERTEBRAL FRACTURE QUANTIFICATION

The present invention relates to a method of deriving an estimate of the extent of fracture in a set of vertebrae.

Osteoporosis is a known metabolic bone disorder and is characterised by a gradual decline in bone mass with age that leads to increased bone fragility and increased risk of vertebral fractures. An important factor used in the evaluation of osteoporosis is that of vertebral fractures. Early detection of developing fractures leads to increased under-standing of disease progress and to earlier improved treatment of individual patients. It is known that diagnosis of vertebral fractures can be difficult and a substantial portion of existing vertebral fractures do not come to clinical attention and remain undiagnosed and untreated.

Radiographic diagnosis of vertebral fractures is considered to be the best way to identify and confirm their presence and numerous methods have been proposed to quantify vertebral body shape and to identify deformities. The diagnostic methods can be divided into two categories: quantitative and semi-quantitative assessment, although some methods possess features from both approaches.

The known quantitative morphometric methods use fixed point placement and well defined fracture definitions. Usually 6 points are drawn manually on a radiograph to derive, for example, anterior height, middle height, and posterior height. From the relationships between the various heights, different ratios can be calculated. One known algorithm defines vertebral fracture as present if any of the ratios falls 3 SD below a specific mean ratio of vertebrae in women. A specific ratio is predetermined for each vertebra to classify it as fractured or not. For example, a vertebra may be classified as having a wedge fracture if T4 has a 17% deformity in comparison to the specific ratio or if T5 has a 22% deformity in comparison to the specific ratio. Another known method defines vertebral fracture if any of the heights of the vertebrae between T5 and L5 divided by the height of vertebra T4 falls below 3 SD below the vertebra specific mean ratio in normal women. If T4 is fractured, T5 is used as reference instead. A further known method calculates, for a given vertebra, the mean predicted posterior height from the measured height of four adjacent vertebrae and the mean posterior height of the given vertebrae and four adjacent vertebrae in normal women.

Each of these quantitative methods has several limitations. The quantitative method involving placement of points on the vertebrae is subjective and small subjective differences in point placement introduces variability into the process of detecting vertebral fractures and thereby limits the reproducibility of the measurement. The quantitative methods described show considerable variants in fracture sensitivity and specificity. Secondly, manual placement of points is laborious and time consuming. Third, by only using a limited number of height points marked on each vertebra there is the possibility that some information may be lost. The height points marked on each vertebra do not completely describe its shape and this may change a lot more subtly with osteoporosis than the height measurements.

Semi-quantitative morphometry methods are also known. The concept behind this idea is that semi-quantitative morphometry may be used to distinguish an osteoporotic change in vertebral height from another disease. A known semi-quantitative method grades the vertebrae into a few categories based on visual inspection and without direct vertebral measurements. The vertebrae are graded as normal (grade 0), mildly deformed (grade 1: reduction of 20 to 25 percent of height and 10 to 20 percent of apparent vertebral area), moderately deformed (grade 2: reduction of 25 to 40 percent of height and 20 to 40 percent of apparent vertebral area), and severely deformed (grade 3: reduction of more than 40 percent of height and apparent vertebral area). In addition to the height reductions, alterations in the shape relative to adjacent vertebrae and expected normal appearance are taken into account. These methods however have limited sensitivity and the classification could in borderline cases rather arbitrarily be considered normal or fractured.

Smyth et al (Radiology, May 1999, pp 571-578) compare a given vertebra shape, as observed in the image, directly to vertebra shapes found in other images to decide whether this given vertebra is fractured or not. The decision is obtained using a statistical classifier that is trained on examples of healthy and fractured vertebrae to distinguish between the two classes. This method models shape variability as seen in different images but ignores the shape of the other vertebrae in the same subject.

The present invention seeks to provide an estimate of the extent of fracture in a set of vertebrae more accurately than the above described methods by comparing the full vertebral shape with mathematical models of normal vertebrae and using neighbouring vertebrae as predictors of the unfractured shape of verterbrae under study.

Accordingly, the present invention provides a method of deriving an estimate of the extent of fracture in a vertebra by processing an image of part of a spine, comprising the steps of segmenting the image of at least two vertebrae in the spine to obtain data representative of the shape and size of each of the vertebrae; reconstructing an approximation of the shape of a first of the vertebrae by comparing the data obtained for a second of the two vertebrae with a mathematical model of at least the same two vertebrae of an unfractured spine; adapting the second vertebra in the model to fit the second imaged vertebra with consequent changes to the remainder of the model; and predicting the unfractured shape and size of the first vertebra using the first vertebra of the adapted model; comparing the shape and size of the first vertebra as imaged with the predicted unfractured shape and size of the first vertebra; and computing the difference between the respective images to obtain a result representative of the extent of fracture in the first vertebra.

Preferably, the method further comprises the steps of reconstructing an approximation of the shape and size of the second vertebra by: comparing the data obtained for the first vertebra with the mathematical model; adapting the first vertebra in the model to fit the first imaged vertebra with consequent changes to the remainder of the model; and predicting the unfractured shape and size of the second vertebra using the second vertebra of the adapted model; comparing the shape and size of the second vertebra as imaged with the predicted unfractured shape and size of the second vertebra; and computing the differences between the respective images of the first and second vertebrae to obtain a result representative of the extent of fracture in the set of vertebrae.

Preferably, the method further comprises segmenting the images of a third to nth vertebrae in the image of the spine to obtain data representative of the shape and size of the third to nth vertebrae; reconstructing further approximations of the shape and size of the first vertebrae by: comparing the data for the third vertebra with a mathematical model of at least the same n vertebrae of an unfractured spine; adapting the third vertebra in the model to fit the third imaged vertebra with consequent changes to the remainder of the model; and predicting the unfractured shape and size of the first vertebra using the first vertebra of the adapted model.

In a preferred embodiment, the method further comprises reconstructing an approximation of the shape and size of each of the n vertebrae by: comparing each of the n vertebrae in turn with the mathematical model; adapting the mathematical model to each of the other n−1 vertebrae in turn to obtain n−1 predictions of each of the vertebrae; processing the n−1 predictions of the unfractured shape and size of each vertebrae to obtain a single prediction of the unfractured shape and size of each of the n vertebrae; comparing the shape and size of each vertebra as imaged with the single predicted unfractured shape and size of the vertebra; computing the difference between the respective images to obtain a result representative of the extent of fracture in the set of vertebrae.

The present invention also extends to an instruction set for deriving an estimate of the extent of fracture in a vertebra of a processed image of part of a spine, the instruction set comprising instructions for segmenting the image of at least two vertebrae in the spine to obtain data representative of the shape and size of each of the vertebrae; reconstructing an approximation of the shape of a first of the vertebrae by comparing the data obtained for a second of the two vertebrae with a mathematical model of at least the same two vertebrae of an unfractured spine; adapting the second vertebra in the model to fit the second imaged vertebra with consequent changes to the remainder of the model; and predicting the unfractured shape and size of the first vertebra using the first vertebra of the adapted model; comparing the shape and size of the first vertebra as imaged with the predicted unfractured shape and size of the first vertebra; and computing the difference between the respective images to obtain a result representative of the extent of fracture in the first vertebra.

The present invention also extends to a data processor for deriving an estimate of the extent of fracture in a vertebra of a processed image of part of a spine, having stored therein an instruction set comprising instructions for segmenting the image of at least two vertebrae in the spine to obtain data representative of the shape and size of each of the vertebrae; reconstructing an approximation of the shape of a first of the vertebrae by comparing the data obtained for a second of the two vertebrae with a mathematical model of at least the same two vertebrae of an unfractured spine; adapting the second vertebra in the model to fit the second imaged vertebra with consequent changes to the remainder of the model; and predicting the unfractured shape and size of the first vertebra using the first vertebra of the adapted model; and comparing the shape and size of the first vertebra as imaged with the predicted unfractured shape and size of the first vertebra; and computing the difference between the respective images to obtain a result representative of the extent of fracture in the first vertebra.

Preferably, the mathematical model of the vertebrae used in all the above aspects of the invention is a point distribution model (PDM). The concept and practice of PDMs is described in the literature, see for instance T. Cootes, C. Taylor, D. Cooper, and J. Graham, 'Active Shape Models—their training and application' CVIU 61(1), pp 38-59, 1995. In a PDM, the shape and deformation of an object can be expressed statistically by formulating the shape as a vector representing a set of points that describe the object. This shape and its deformation (expressed within a training set, indicative of the object deformation) can then be learnt through a statistical analysis. An example of the previous application of a PDM model to the segmentation of vertebrae is to be found in Zamora et al (SPIE 2000: "Hierarchical Segmentation of Vertebrae from X-ray Images"). A further example is to be found in Smyth et al (above).

Embodiments of the present invention will hereinafter be described, by way of example, with reference to the accompanying drawings, in which.

The method of deriving an estimate of the extent of fracture in a set of vertebrae from x-ray images of a spine as proposed in the preferred practice of the present invention consists of four steps.

The first step is to construct a mathematical model that provides an indication of what unfractured vertebrae should look like.

The mathematical model is arranged to be built from a collection of x-ray images of sets of unfractured vertebrae. First, each of the vertebrae in the respective images is segmented. It will be appreciated that this can be done using an automated, semi automated or manual method.

The segmented vertebrae are then individually aligned, to remove translational and rotational variance from the shape. A specific example is given below and is described with reference to the use of generalized Procrustes Analysis. However, it will be appreciated that any known standard technique could be used to achieve the same effect.

The aligned shapes are then used to construct the mathematical model of vertebrae of a normal spine. The mathematical model can be based on classical linear regression or more advanced techniques, for example, non-linear regression. The example below describes the use of multivariate multiple linear regression.

The second step in the preferred method is to predict the shape of a normal vertebra, i.e. a vertebra without fracture, using the mathematical model. An x-ray image of a set of vertebrae is processed, where one or more of the vertebrae may be fractured. To quantify the vertebrae in an image, the vertebrae are first segmented and then aligned (as described above). The aligned shape is then used as an input to the mathematical model. For example, a specific vertebra, for example L1($a$) (shown in FIG. 1) is compared to the corresponding vertebra, L1($b$), of the mathematical model. The mathematical model is then adapted to "match" the data of input vertebra L1($a$). By virtue of adapting the mathematical model to match L1($b$) as required, a corresponding adjustment is also made in the model to each of the other vertebrae in the spine. The mathematical model can then be used to predict the shape and size of all other vertebrae for which a prediction may be required. Typically, the mathematical model is applied pair wise to each other vertebra in the image, that is to each of the vertebrae neighbouring L1($a$) and ($b$).

In an image having n vertebrae, each vertebra can be predicted n−1 times.

The third step of the preferred method of the invention is to reconstruct the true normal shape, that is, the shape of the vertebra, for example, L1($a$) prior to fracture. Thus, based on the multiple predictions of all the vertebrae, a probabilistic estimate of the true shape of each vertebra may be derived. In the example given below, use of an EM algorithm (Expectation-Maximization: see A. P. Dempster, N. M. Laird, D. B. Rubin: "Maximum Likelihood from Incomplete Data via the EM Algorithm", Journal of the Royal Statistical Society, Series 13, 39:34-37, 1977) is described. The reconstructed shape is a probabilistic estimate of how the vertebra would look if it were not fractured.

The fourth and final step of the preferred method of the present invention is to quantify the extent of vertebral fracture based on a comparison between the reconstructed shape and the actual image.

It will be appreciated that the image used for the comparison may be the image used to obtain the prediction or any other image of the same set of vertebrae. In particular, the image to be compared may be obtained from a subsequent scan of the same set of vertebrae.

The reconstructed shape can be used to derive an estimate of the extent of fracture of a vertebra by comparing the shape of the segmented vertebra with that of the reconstructed shape. The estimate can be based on any known method of determining fracture quantification, statistical shape similarity, or physical measures, for example, change in area, change in height, corner and/or midpoint height changes, Mahalanobis distance, spatial overlap, boundary differences, comparison of the full shape, energy needed to compress a vertebra, etc.

The above steps, up to reconstruction of a normal vertebra, will now be described with reference to a specific example.

Figure 1:
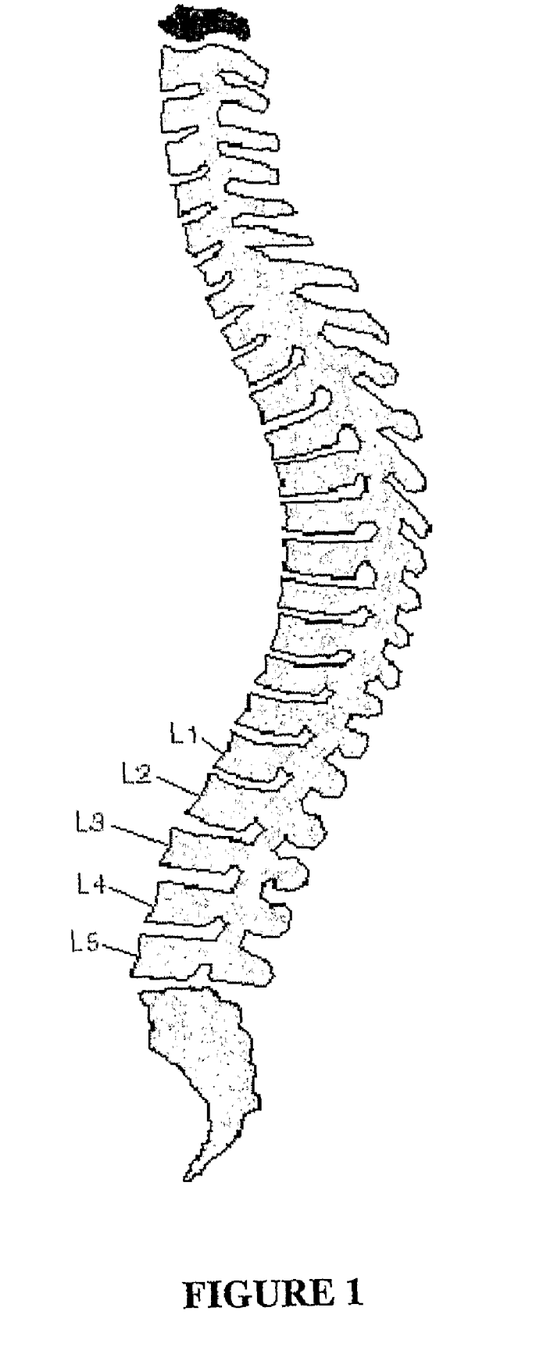
FIG. 1 shows an exemplary view of a spine, indicating the respective positions of different vertebrae.

The mathematical model can be constructed by setting up a shape model, in the present invention, based on a suitably large number (we have used 86) lateral lumbar radiographs of the spine. It will be appreciated that if more images are used, the precision and stability of the model increases. FIG. 1 shows the positioning of different vertebrae in the spine. Preparation of the shape model will be described in relation to L1, L2, L3 and L4.

The vertebral body of L1 through L4 should be manually annotated by a medical expert using a variable number of unlabelled pseudo-landmarks. At least six landmarks are required to detect fractures. If more landmarks are used, the shape of the vertebra is described more clearly. In this manual annotation procedure, a variable number of landmarks are used to ease the burden of the medical expert annotating the vertebrae.

Figure 2:
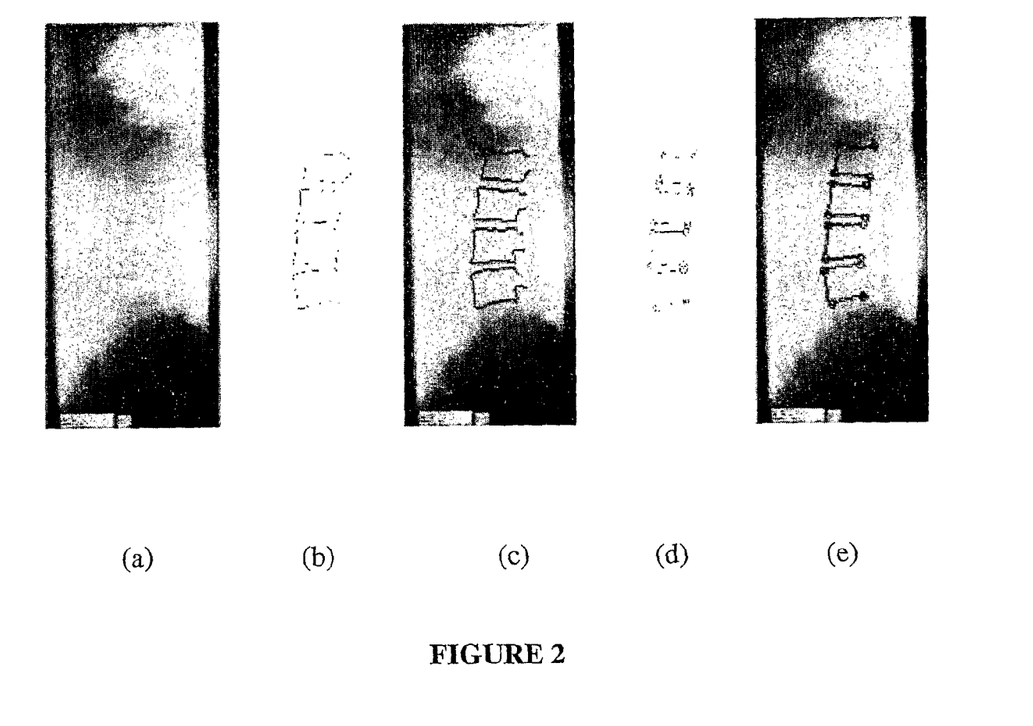
FIGS. 2a to e illustrate the different stages in setting up a shape model of the present invention.

For constructing the shape model, the vertebral body of L1 through L4 should be annotated with a set of finite landmarks points that correspond to specific subjects, for example, the upper left corner, and denote the same anatomical points in different instances. As shown in FIG. 2, for each of the four vertebrae in the annotation a shape model is constructed such that each vertebra is described using 4 anatomical landmarks (corners of the vertebral body) and 21 equidistantly spaced intermediate pseudo-landmarks that do not correspond to a specific subject. Landmarks are labeled in a specific order, for example, the upper right landmark is typically the first landmark in the shape. The corner points are defined as the points closest to the line from the vertebral center of gravity to the anterior and posterior height points annotated by the medical expert. Corresponding landmarks can either be positioned manually or can be derived from the vertebra contours obtained from manual, semi-automatic, or automatic vertebra segmentation. Starting from a contour, corresponding points can be found using a minimum description length (MDL) criterion or, for example, by defining the four corner points, manually or by searching for the points of maximum contour curvature and subsequently interpolating a fixed number of landmarks along the contour between the corner points to derive the equidistantly spaced pseudo landmarks.

Specifically, the vertebra shape outlines and shape variation are described using a point distribution model (PDM). PDMs are used to describe object shapes using a set of corresponding points (landmarks) on each object. In a two-dimensional case each object can be represented as a 2N-dimensional vector of landmarks coordinates:

$$v = (x_1, x_2, \ldots, x_n, u_1, u_2, \ldots, y_n)^T$$

All vertebrae shapes, for example all L1s, are aligned on top of each other so that the differences in their coordinates denote only shape differences and not differences in positioning of the vertebra in the image. Alignment is performed by minimizing the sum of squared distances between all corresponding landmarks on different shapes, i.e. by minimizing the sum of squared differences between the shape vectors.

In this example, the vertebrae outlines in the shape model are individually aligned preferably using generalized Procrustes Analysis to remove translational and rotational variance from the shape. The complex representation of an annotation shape can be defined as:

$$w_i = (x_1 + i^* y_1, x_2 + i^* y_2, \ldots, x_n + i^* y^n)^T$$

and generalised Procrustes alignment can be expressed as $$\omega_i^P = \omega^*_i \hat{\mu} \omega_i / \omega^*_i \omega_i, \ i = 1, 2, \ldots n,$$

where each $\omega_i^P$ is the full Procrustes fit of $\omega_i$ onto $\hat{\mu}$. The full Procrustes estimate of the mean shape [$\mu$] can be found as the eigenvector corresponding to the largest eigenvalue of the complex sum of squares and products matrix:

$$S = \sum_{i=1}^{n} w_i w_i^* / w_i^* w_i \quad i = 1, 2, \ldots n.$$

As set out above, the second step in the method of the present invention is to predict the shape of a normal vertebra, i.e. a vertebra without fracture.

Three regression models are defined for each of the four shape models (vertebrae), based on each neighbouring vertebra.

Regression analysis imposes a model where the response variables (the landmarks of the vertebrae to predict) are a linear function of predictor variables (the landmarks of the vertebrae to predict from) and adjusts the parameters of the model to provide an optimal match of the observed data.

Regression analysis is a conceptually simple method for investigating functional relationships among variables. The relationship can be expressed in the form of an approximation model connecting the response and predictor variables. If we denote the response variable by y and the predictor variable with x, the true relationship between y and x can be approximated by the regression model $$y = f(x) + \epsilon,$$

where $\epsilon$ is assumed to be the random error representing the discrepancy in the approximation.

In this simplest case, the predictor variable (x) and response variable (y) are connected by a line in 2 dimensions, which is fitted to the data. This line forms the model. Once the model is formed, every "predictor" value is directly related to one "response" value, such that every x is associated with one y. This holds for all possible predictor values, not only the ones that were in the observed data.

In univariate multiple linear regression cases with a given vector of inputs:

$$X=(X_1, X_1, \ldots, X_p),$$

the output Y can be predicted via the regression equation $$Y = \beta_0 + \beta_1 X_1 + \beta_2 X_2 + \ldots + \beta_p X_p + \epsilon = \beta_0 + \sum_{i=1}^{P} X_i \beta_i + \epsilon.$$

There exist many different methods for fitting the linear model to a training set; the most common of which is the least-squares method, where the $\beta=(\beta_0, \beta_1, \ldots, \beta_p)^T$ coefficients are chosen so that the residual sum of squares RSS($\beta$) is minimized $$RSS(\beta) = \sum_{i=1}^{n} (y_i - x_i \beta)^2.$$

The equivalent matrix notation is $$RSS(\beta) = (y - X\beta)^T (y - X\beta).$$

The minimization problem can be solved by differentiating RSS with respect to $\beta$ and setting it equal to zero which gives the normal equations $$\frac{\partial RSS}{\partial \beta} = -2X^T (y - X\beta) = 0.$$

Assuming that X is nonsingular, and hence $X^T X$ positive definite, the unique solution is $$\hat{\beta} = (X^T X)^{-1} X^T y.$$

In the multivariate case there are multiple response variables
$$Y_1, Y_2, \ldots, Y_k$$
that need to be predicted from the multiple predictor variables
$$X_0, X_1, \ldots, X_p$$
Assuming a linear model for each response one gets $$Y_k = \beta_{0k} + \sum_{j=1}^{P} X_j \beta_{jk} + \epsilon_k$$

The least squares estimates have the same form as the univariate regression $$\hat{B} = (X^T X)^{-1} X^T Y.$$

The regression coefficients for the kth response are just the least squares estimates in the regression of $y_k$ on $x_0, x_1, \ldots, x_p$. Multiple responses do not affect one another's least squares estimates.

In models with many variables often stability problems occur, due to multicollinearity; the independent variables are strongly correlated and exclusion of an observation can markedly change the estimates. When multicollinearity occurs, least squares estimates are unbiased, but their variances are large so they may be far from the true value.

The simplest solution to prevent harmful multicollinearity is the removal of some of the correlated predictor variables from the regression model. The rationale for this approach is that highly correlated variables imply redundant information that may be removed without impairing the ability to predict the response variable. Various methods exist to remove the redundant variables and only retain those that contribute to explaining the variance of the response variable, but the problem with these methods are that they rely on the same principles (standard errors of the estimates) that results in variance inflation. Thus it might not be possible to objectively select the predictor variables to remove. Moreover, all the predictor variables might be important. Even though the variables are highly correlated they provide additional information that could improve the performance of the response variable.

The least squares estimate of the parameters $\beta$ have the smallest variance of all unbiased estimates, there may however exist biased estimators with a smaller mean square error. One of the solutions to the multicollinearity problem is ridge regression. In ridge regression a little bias is traded for a large reduction in variance. The ridge regression estimate for $\beta$ is $$\hat{\beta}^{ridge} = (X^T X + \lambda I)^{-1} X^T Y,$$

where I is the p×p identity matrix and $-\leq \lambda \leq 1$ is a regularization parameter. It is assumed that the predictor variables are scaled so that $X^T X$ is in the correlation form. The solution adds a positive constant to the diagonal of $X^T X$ before inversion. This makes the problem nonsingular, even if $X^T X$ is not of full rank.

Figure 3:
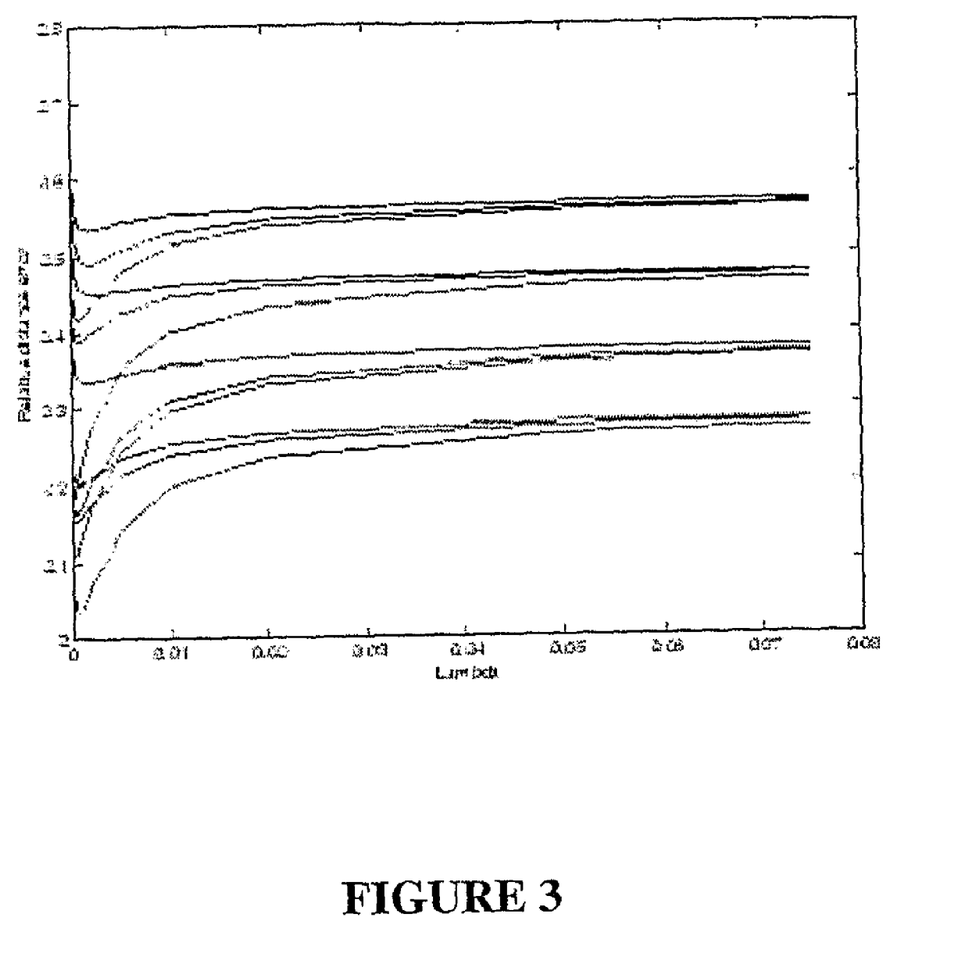
FIG. 3 shows a graph of relative distance error against lambda illustrating the prediction error of 12 shape regression models described in the present invention.

As shown in FIG. 3, for each of the 12 regression models the shape regression models estimation error $E(\lambda)$ can be calculated using leave one out cross-validation. The estimation error can be defined as the average distance from the predicted shape points to the outline of the corresponding original shape relative to the height of the average vertebra. The result of this specific example is shown in FIG. 3.

Figure 4:
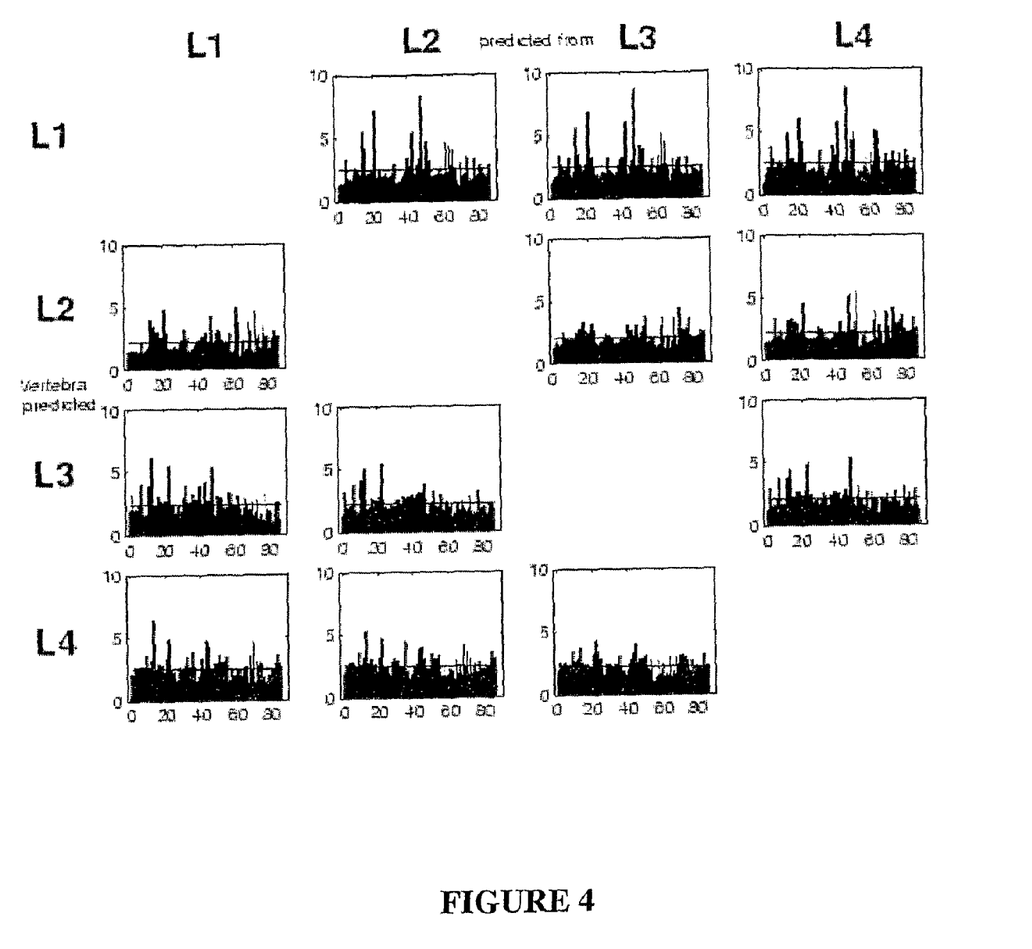
FIG. 4 illustrates a prediction error of shape regression using optimal ridge regression coefficient described in the present invention.

Based on experimental analysis, it has been deduced that when $\lambda=0$ (ordinary least squares estimation) the regression models are unstable; the models were numerical singular. The optimal value for the entire data set was found to be $\lambda = 5*10^{-4}$. With this optimal ridge regression coefficient, the relative average prediction error of one prediction is found to be between 1.5 and 9%. As shown in FIG. 4, the average prediction error over the whole dataset is approximately 2.5%.

Figure 5:
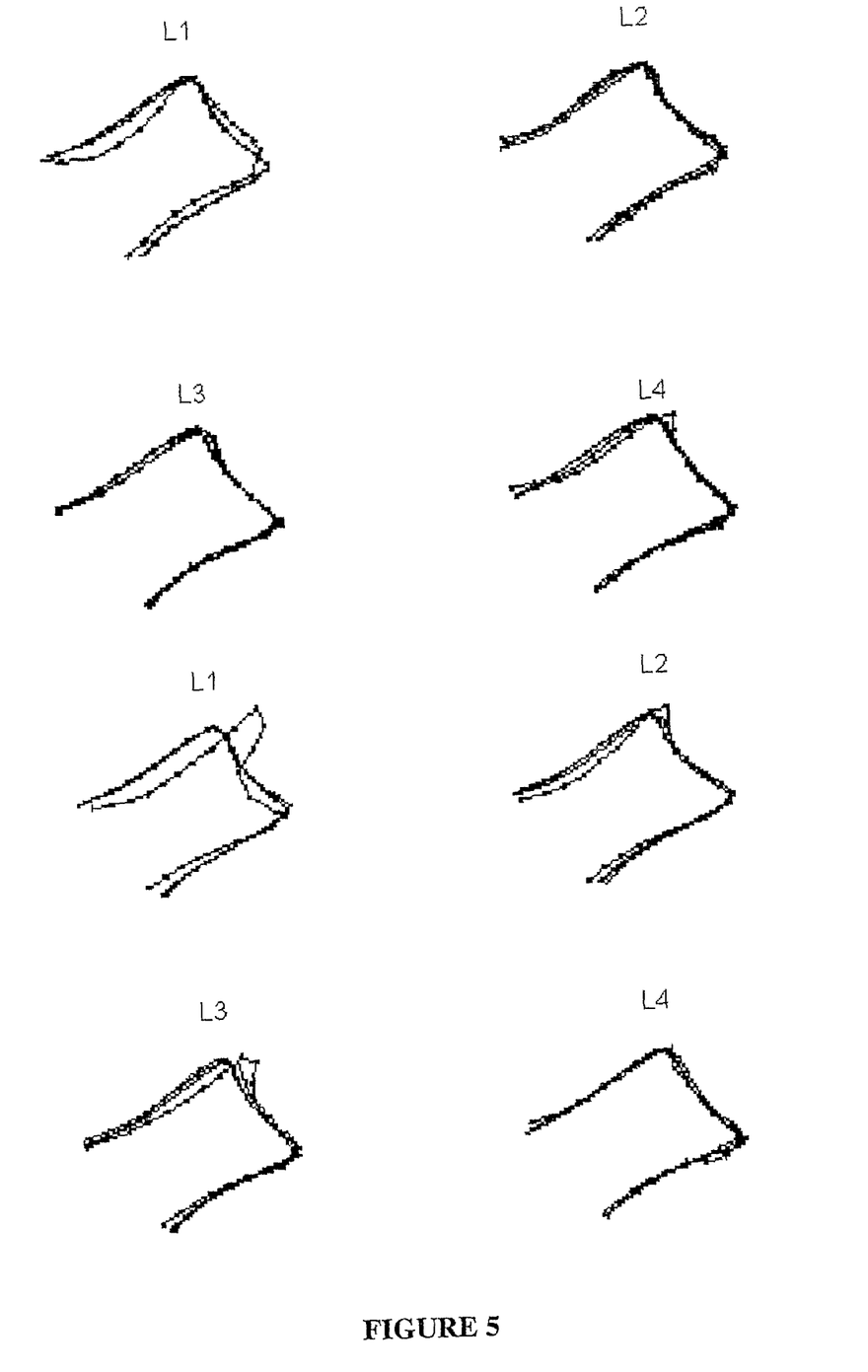
FIG. 5 shows the results of predictions based on two datasets that were used to compile the original mathematical model of the present invention The present invention will hereinafter be described with particular reference to the analysis of x-ray images of vertebrae of a spine. It will, however, be appreciated that the described method could be applied to other medical images of a spine for example, DXA, Computer Tomography (CT) or Magnetic Resonance.

FIG. 5 shows the results of predictions based on two datasets that were used to compile the original mathematical model. In both datasets there can be seen a large prediction error when predicting the lumbar vertebra L1. In both these cases, the prediction errors are due to shape deformities in the original shape of the corresponding vertebrae.

To obtain a more accurate prediction, it is preferable to combine the multiple prediction of one vertebra into a single prediction using, for example, an Expectation-Maximization algorithm. The algorithm is used to consider a collection of reconstructions to compute a probabilistic estimate of a true reconstruction and measure the performance level represented by each construction. Specifically, the algorithm considers a collection of segmentations, in this case of the predicted vertebrae, and computes a probabilistic estimate of the true segmentation, by estimating an optimal combination of the segmentations.

Alternatively, each of the predictor vertebrae could be weighed by its respective probability, where the probability is either determined from the shape of the predictor vertebrae in relation to the shape model, or from its fit with the image data, or both. Subsequently, these results could be used to compute a weighted average, thus resulting in a single prediction.

It will be appreciated that there are many known methods of comparing an image of a vertebra having a suspected fracture, with an image of an apparently "normal" vertebra. These methods have therefore not been described in detail.

In the above described procedure, the statistical model has been validated by using it to predict the shapes of vertebrae belonging to one of the images on which it was itself based. In clinical practice, one would apply the model to a further spinal image obtained from a patient. For each of the vertebrae in the patient's image, the vertebrae would be segmented using an automated, semi automated or manual method and then would be individually aligned to remove translational and rotational variance from the shape, as described above.

The statistical model would then be applied to each vertebra to predict its unfractured shape on the basis of each of the other vertebra in the image, providing n−1 predictions for a set of n vertebrae. From the n−1 predictions, the best single prediction would be deduced for each vertebra. Comparison with the actual imaged shape in each case will provide a quantified estimate of degree of fracture on a continuous scale. Thus, it can be seen that the example of the invention uses a model of shape variability across a population as well as within a single subject. A statistical model of the interrelationships between non-fractured vertebral shapes is derived using shape regression analysis on a population of healthy subjects. Using this model and the known shapes of all other vertebrae in the same subject, one can predict the most likely 'normal' shape of a given vertebra, i.e. the shape that the vertebra is expected to have based on the assumption that it is not fractured. The dissimilarity between this expected shape and the true shape found in the image is a measure of the degree of abnormality of this vertebra. The dissimilarity can be expressed in many ways, for instance as a sum of distances between landmark points on both shapes, as a measure of shape overlap, or as a probability obtained from a classifier.

Information about the predicted shape of a vertebra obtained from an initial scan could also be used to enhance a later prediction of the same vertebra when using a subsequent scan. In this case, information from a previous prediction could be used in addition to the n−1 predictions obtained from the statistical model. This would be particularly useful in the case where, for example, one or more vertebrae in a subsequent scan have significantly deteriorated. In this respect, if more than one vertebrae is fractured, using information from a previous scan would help ensure that this and any subsequent predictions would provide a more realistic prediction of what the vertebra may have looked like before fracture.

It is also possible to compare the results obtained from subsequent scans to give a measure of fracture. This would also enable the shape changes between two or more scans of the same vertebra (or vertebrae) to be modelled to chart progress.

Results of a scan may also be used to predict future fractures. If a model charting progressive deterioration in vertebrae is prepared, it would be possible to use information derived from a comparison of subsequent scans to assess the potential risk of fracture in the future. In this respect, any difference found in subsequent scans could be compared with a mathematical model of vertebrae with progressive fractures to assess the risk that the present vertebra may become fractured.

It will be appreciated that the above described method may be applied to vertebrae throughout the thoracic or lumbar regions of the spine.

It will be appreciated that modifications of, and alterations to, the embodiments as describe and illustrated may be made within the scope of this application.

The invention claimed is:

1. A method of deriving an estimate of the extent of fracture in a vertebra by processing an image of part of a spine, comprising the steps of:
   segmenting the image of at least two vertebrae in the spine to obtain data representative of the shape and size of each of the vertebrae;
   reconstructing an approximation of the shape of a first of the vertebrae by:
      comparing the shape and size data obtained for a second of the two vertebrae with a mathematical shape and size model of at least the same two vertebrae of an unfractured spine;
      adapting the second vertebra in the model to fit the second imaged vertebra with consequent changes to the remainder of the model; and
      predicting the unfractured shape and size of the first vertebra using the first vertebra of the adapted model;
   comparing the shape and size of the first vertebra as imaged with the predicted unfractured shape and size of the first vertebra; and
   computing the difference between the respective images to obtain a result representative of the extent of fracture in the first vertebra.

2. A method as claimed in claim 1, further comprising the steps of:
   reconstructing an approximation of the shape and size of the second vertebra by:
      comparing the data obtained for the first vertebra with the mathematical model;
      adapting the first vertebra in the model to fit the first imaged vertebra with consequent changes to the remainder of the model; and
      predicting the unfractured shape and size of the second vertebra using the second vertebra of the adapted model;
   comparing the shape and size of the second vertebra as imaged with the predicted unfractured shape and size of the second vertebra; and
   computing the differences between the respective images of the first and second vertebrae to obtain a result representative of the extent of fracture in the set of vertebrae.

3. A method as claimed in claim 1 or claim 2, further comprising the steps of:
   segmenting the images of a third to nth vertebrae in the image of the spine to obtain data representative of the shape and size of the third to nth vertebrae;
   reconstructing further approximations of the shape and size of the first vertebrae by:
      comparing the data for the third vertebra with a mathematical model of at least the same n vertebrae of an unfractured spine;
      adapting the third vertebra in the model to fit the third imaged vertebra with consequent changes to the remainder of the model; and
   predicting the unfractured shape and size of the first vertebra using the first vertebra of the adapted model;
   repeating the steps of adapting and predicting for each of the fourth to the nth vertebra to obtain n−1 predictions of the unfractured shape and size of the first vertebra;
   processing the n−1 predictions of the unfractured shape and size of the first vertebra to obtain a single prediction of the unfractured shape and size of the first vertebra representative of the n−1 predictions;

comparing the shape and size of the first vertebra as imaged with the single predicted unfractured shape and size of the first vertebra; and computing the difference between the respective images to obtain a result representative of the extent of fracture in the set of vertebrae.

4. A method as claimed in claim 3, further comprising the steps of:

reconstructing an approximation of the shape and size of each of the n vertebrae by:

comparing each of the n vertebrae in turn with the mathematical model;

adapting the mathematical model to each of the other n−1 vertebrae in turn to obtain n−1 predictions of each of the vertebrae;

processing the n−1 predictions of the unfractured shape and size of each vertebra to obtain a single prediction of the unfractured shape and size of each of the n vertebrae;

comparing the shape and size of each vertebra as imaged with the single predicted unfractured shape and size of the vertebra; and computing the difference between the respective images to obtain a result representative of the extent of fracture in the set of vertebrae.

5. A non-transitory computer-readable medium encoded with an instruction set for deriving an estimate of the extent of fracture in a vertebra of a processed image of part of a spine, the instruction set comprising instructions for:

segmenting the image of at least two vertebrae in the spine to obtain data representative of the shape and size of each of the vertebrae;

reconstructing an approximation of the shape of a first of the vertebrae including:

comparing the shape and size data obtained for a second of the two vertebrae with a mathematical shape and size model of at least the same two vertebrae of an unfractured spine;

adapting the second vertebra in the model to fit the second imaged vertebra with consequent changes to the remainder of the model; and predicting the unfractured shape and size of the first vertebra using the first vertebra of the adapted model;

comparing the shape and size of the first vertebra as imaged with the predicted unfractured shape and size of the first vertebra; and computing the difference between the respective images to obtain a result representative of the extent of fracture in the first vertebra.

6. A non-transitory computer-readable medium encoded with an instruction set as claimed in claim 5, further comprising instructions for:

reconstructing an approximation of the shape and size of the second vertebra by:

comparing the data obtained for the first vertebra with the mathematical model;

adapting the first vertebra in the model to fit the first imaged vertebra with consequent changes to the remainder of the model; and predicting the unfractured shape and size of the second vertebra using the second vertebra of the adapted model;

comparing the shape and size of the second vertebra as imaged with the unfractured predicted shape and size of the second vertebra; and computing the differences between the respective images of the first and second vertebrae to obtain a result representative of the extent of fracture in the set of vertebrae.

7. A non-transitory computer-readable medium encoded with an instruction set as claimed in claim 5 or claim 6, further comprising instructions for:

segmenting the images of a third to nth vertebrae in the image of the spine to obtain data representative of the shape and size of the third to nth vertebrae;

reconstructing further approximations of the shape and size of the first vertebrae including:

comparing the data for the third vertebra with a mathematical model of at least the same n vertebrae of an unfractured spine;

adapting the third vertebra in the model to fit the third imaged vertebra with consequent changes to the remainder of the model; and predicting the unfractured shape and size of the first vertebra using the first vertebra of the adapted model;

repeating the steps of adapting and predicting for each of the fourth to the nth vertebra to obtain n−1 predictions of the unfractured shape and size of the first vertebra;

processing the n−1 predictions of the shape and size of the first vertebra to obtain a single prediction of the unfractured shape and size of the first vertebra representative of the n−1 predictions;

comparing the shape and size of the first vertebra as imaged with the single predicted unfractured shape and size of the vertebra; and computing the difference between the respective images to obtain a result representative of the extent of fracture in the set of vertebrae.

8. A non-transitory computer-readable medium encoded with an instruction set as claimed in claim 7, further comprising instructions for:

reconstructing an approximation of the shape and size of each of the n vertebrae including:

comparing each of the n vertebrae in turn with the mathematical model;

adapting the mathematical model to each of the n−1 vertebrae in turn to obtain n−1 predictions of each of the vertebrae;

processing the n−1 predictions of the shape and size of each vertebra to obtain a single prediction of the unfractured shape and size of each of the n vertebrae;

comparing the shape and size of each vertebra as imaged with the single predicted unfractured shape and size of the vertebra; and computing the difference between the respective images to obtain a result representative of the extent of fracture in the set of vertebrae.

9. A data processor for deriving an estimate of the extent of fracture in a vertebra of a processed image of part of a spine, having stored therein an instruction set comprising instructions for:

segmenting the image of at least two vertebrae in the spine to obtain data representative of the shape and size of each of the vertebrae;

reconstructing an approximation of the shape of a first of the vertebrae including:

comparing the shape and size data obtained for a second of the two vertebrae with a mathematical shape and size model of at least the same two vertebrae of an unfractured spine;

adapting the second vertebra in the model to fit the second imaged vertebra with consequent changes to the remainder of the model; and predicting the unfractured shape and size of the first vertebra using the first vertebra of the adapted model;

comparing the shape and size of the first vertebra as imaged with the predicted unfractured shape and size of the first vertebra; and computing the difference between the respective images to obtain a result representative of the extent of fracture in the first vertebra.

10. A data processor as claimed in claim 9, having stored therein further instructions for:

reconstructing an approximation of the shape and size of the second vertebra by:

comparing the data obtained for the first vertebra with the mathematical model;

adapting the first vertebra in the model to fit the first imaged vertebra with consequent changes to the remainder of the model; and predicting the unfractured shape and size of the second vertebra using the second vertebra of the adapted model;

comparing the shape and size of the second vertebra as imaged with the predicted unfractured shape and size of the second vertebra; and computing the differences between the respective images of the first and second vertebrae to obtain a result representative of the extent of fracture in the set of vertebrae.

11. A data processor as claimed in claim 9 or claim 10, having stored therein further instructions for:

segmenting the images of a third to nth vertebrae in the image of the spine to obtain data representative of the shape and size of the third to nth vertebrae;

reconstructing further approximations of the shape and size of the first vertebrae including:

comparing the data for the third vertebra with a mathematical model of at least the same n vertebrae of an unfractured spine;

adapting the third vertebra in the model to fit the third imaged vertebra with consequent changes to the remainder of the model; and predicting the unfractured shape and size of the first vertebra using the first vertebra of the adapted model;

repeating the steps of adapting and predicting for each of the fourth to the nth vertebra to obtain n−1 predictions of the unfractured shape and size of the first vertebra;

processing the n−1 predictions of the shape and size of the first vertebra to obtain a single prediction of the shape and size of the first vertebra representative of the n−1 predictions;

comparing the shape and size of the first vertebra as imaged with the single predicted unfractured shape and size of the vertebra; and computing the difference between the respective images to obtain a result representative of the extent of fracture in the set, of vertebrae.

12. A data processor as claimed in claim 11, having stored therein further instructions for:

reconstructing an approximation of the shape and size of each of the n vertebrae including:

comparing each of the n vertebrae in turn with the mathematical model;

adapting the mathematical model to each of the n−1 vertebrae in turn to obtain n−1 predictions of each of the vertebrae;

processing the n−1 predictions of the shape and size of each vertebrae to obtain a single prediction of the unfractured shape and size of each of the n vertebrae;

comparing the shape and size of each vertebra as imaged with the single predicted unfractured shape and size of the vertebra; and computing the difference between the respective images to obtain a result representative of the extent of fracture in the set of vertebrae.

* * * * *